(12) United States Patent
Chang et al.

(10) Patent No.: US 12,428,398 B2
(45) Date of Patent: Sep. 30, 2025

(54) 2-(2,4,5-SUBSTITUTED PHENYLAMINO) PYRIMIDINE DERIVATIVE AND CRYSTALLINE FORM B THEREOF

(71) Applicant: Henan Genuine Biotech Co., Ltd., Pingdingshan (CN)

(72) Inventors: Junbiao Chang, Pingdingshan (CN); Jinfa Du, Pingdingshan (CN); Kaikai Zhu, Pingdingshan (CN); Kai Wang, Pingdingshan (CN); Jianyong Li, Pingdingshan (CN); Chunxia Zhang, Pingdingshan (CN); Dongxu Yi, Pingdingshan (CN)

(73) Assignee: HENAN GENUINE BIOTECH CO., LTD., Pingdingshan (CN)

( * ) Notice: Subject to any disclaimer, the term of this patent is extended or adjusted under 35 U.S.C. 154(b) by 964 days.

(21) Appl. No.: 17/497,994

(22) Filed: Oct. 11, 2021

(65) Prior Publication Data

US 2022/0024897 A1    Jan. 27, 2022

Related U.S. Application Data

(63) Continuation-in-part of application No. PCT/CN2019/081902, filed on Apr. 9, 2019.

(51) Int. Cl.
*C07D 403/04*    (2006.01)
(52) U.S. Cl.
CPC ........ *C07D 403/04* (2013.01); *C07B 2200/05* (2013.01); *C07B 2200/13* (2013.01)

(58) Field of Classification Search
CPC .............. C07D 403/04; C07B 2200/05; C07B 2200/13
See application file for complete search history.

(56) References Cited

FOREIGN PATENT DOCUMENTS

| CN | 110003183 A | * | 7/2019 | ........... A61K 31/506 |
| WO | WO-2017117070 A1 | * | 7/2017 | ........... A61K 31/035 |

* cited by examiner

*Primary Examiner* — John S Kenyon
*Assistant Examiner* — Sara Elizabeth Bell
(74) *Attorney, Agent, or Firm* — MATTHIAS SCHOLL P.C.; Matthias Scholl

(57) ABSTRACT

A 2-(2,4,5-substituted phenylamino) pyrimidine derivative, having the following chemical formula I:

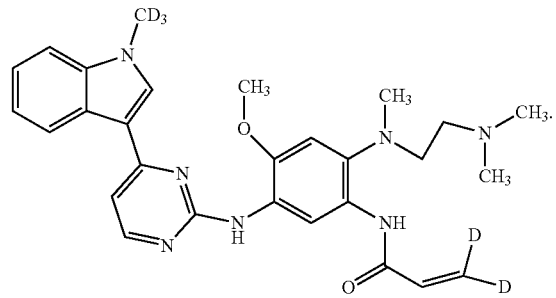

The pyrimidine derivative is useful for treating non-small cell lung cancer.

3 Claims, 5 Drawing Sheets

2-(2,4,5-SUBSTITUTED PHENYLAMINO) PYRIMIDINE DERIVATIVE AND CRYSTALLINE FORM B THEREOF

TECHNICAL FIELD

The disclosure relates to the field of pharmaceutical chemistry, and more particularly to an anti-lung cancer drug, specifically, a 2-(2,4,5-substituted phenylamino) pyrimidine derivative and a crystalline form B thereof.

BACKGROUND

Lung cancer is one of the malignant tumors with the highest morbidity and mortality. About 1.6 million people die of this kind of cancer every year all over the world. In 2017, there are about 800000 lung cancer patients in China. Non-small cell lung cancer (NSCLC), as the most common type of lung cancer, accounts for about 85% of lung cancer cases. In recent years, the diagnosis and treatment of non-small cell lung cancer (NSCLC) has improved significantly. With the arrival of the era of precision medicine for non-small cell lung cancer, it is a popular trend to select a corresponding targeted drug therapy according to the genetic characteristics of patients with lung cancer. Especially in the treatment of advanced non-small cell lung cancer, targeted drugs play an important role. Epidermal growth factor receptor (EGFR) is the most common gene mutation in patients with non-small cell lung cancer, and the corresponding targeted drug EGFR-TKI has been on the market for many years. Conventionally, EGFR-TKI is currently divided into three generations: the first generation is Gefitinib tablets, Erlotinib hydrochloride tablets and Icotinib hydrochloride tablets; the second generation includes Afatinib and Dacomitinib; the third generation is Osimertinib on the market. In general, patients with advanced non-small cell lung cancer will be treated with the first generation EGFR-TKI after EGFR mutation is confirmed by gene detection. Unfortunately, almost all patients taking EGFR-TKI will be resistant against drugs in the end, and one reason for drug resistance is due to T790M mutation. Therefore, overcoming the drug resistance caused by T790M mutation is the purpose of the new generation of EGFR-TKI, of which Osimertinib is the leader. Osimertinib is developed by AstraZeneca, and the R&D stage code is AZD9291. In March 2017, the State Food and Drug Administration approved the import application of Osimertinib, only one year and four months away from the first approval in the world. The approval process for the listing of Osimertinib in China took only 7 months, which reflected the urgency of patients' needs. However, the N-methyl of indole of Osimertinib is easily oxidized by cytochrome P450 in vivo to produce demethylated Osimertinib (AZ5104, below). The inhibitory activity of AZ5104 on wild EGFR was 14.5 times stronger than that of Osimertinib, while the anticancer activity was only 7.5 times stronger. Moreover, the inhibitory effect on wild EGFR is considered to be related to the occurrence of toxic and side effects such as rash after treatment (J. Med. Chem. 2014, 578249). Therefore, it is still necessary to find new drugs for the treatment of lung cancer with stronger anticancer activity and less toxic and side effects.

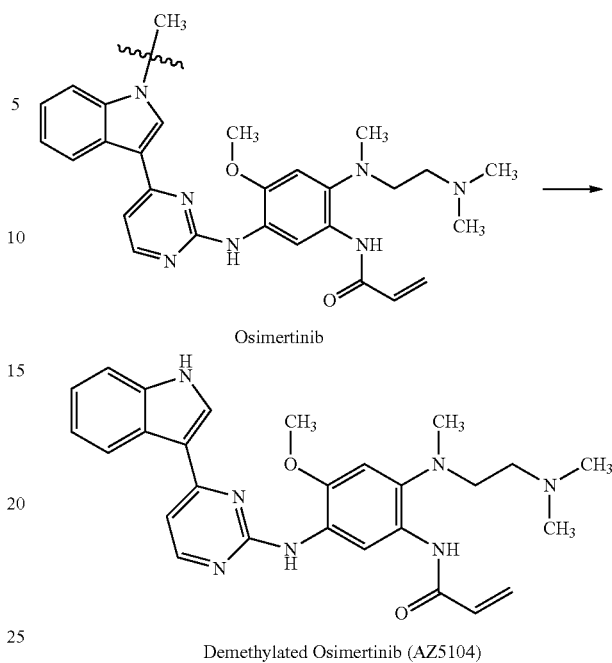

Osimertinib

Demethylated Osimertinib (AZ5104)

Henan Mattel Bio Pharmaceutical Co Ltd. has developed a series of new drugs of 2-(2,4,5-substituted phenylamino) pyrimidine derivatives and applied for a patent "2-(2,4,5-substituted phenylamino) pyrimidine derivatives, their preparation method and their application in the preparation of antitumor drugs" (2017112825988). To find compounds with better biological activity, the compounds are further modified.

SUMMARY

One objective of the disclosure is to provide an anti-lung cancer drug, that is, a 2-(2,4,5-substituted phenylamino) pyrimidine derivative I and a crystalline form B thereof. The compound I is Dositinib for short.

To achieve the above objective, the following technical solutions are adopted.

The chemical name of Dositinib is N-(2-(((2-(Dimethylamino) ethyl)) (methyl) amino)-4-methoxy-5-((4-(d3-1-methyl-1H-indol-3-yl) pyrimidin-2-yl) amino) phenyl) d2-acrylamide-mesylate, and the chemical structure is as follows:

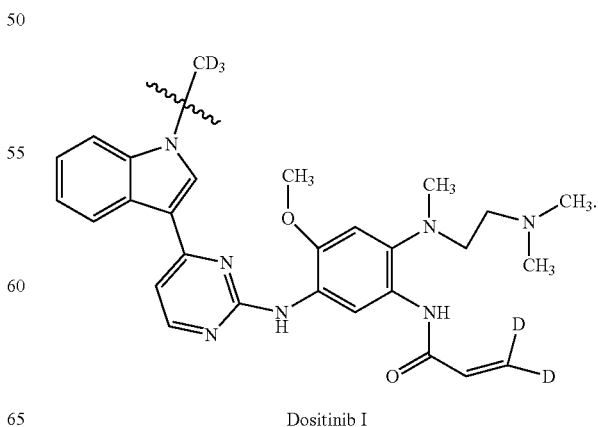

Dositinib I

The preclinical animal pharmacokinetic and pharmacodynamic studies found that the production of the metabolite AZ5104-2D of N-demethylation of indole of Dositinib was 98% (male) and 83% (female) lower than that of AZ5104 of Osimertinib (see FIGS. 2-5 and Table 1), which was conducive to reducing the toxic and side effects caused by inhibiting wild EGFR.

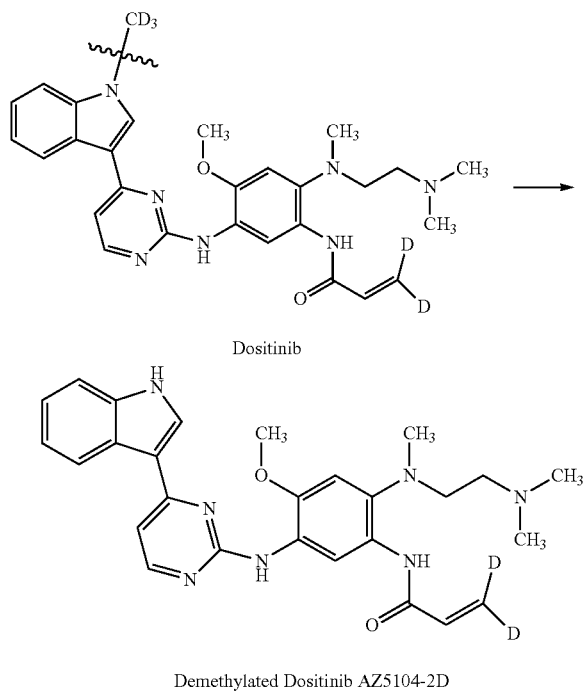

Dositinib

Demethylated Dositinib AZ5104-2D

TABLE 1

| | Pharmacokinetics of Dositinib and AZD9291 in rats | | | | |
|---|---|---|---|---|---|
| | Male/female | | Male/female | | Male/female |
| Rats Drug | Dositinib (crystalline form B) | AZ5104-2D | AZD9291 (crystalline form A + B) | AZ5104 | Dositinib (crystalline form A + B) |
| Cmax (ng/mL) | 115/208 | 0.256/ 0.813 | 106/207 | 10.8/ 5.79 | 110/205 |
| T1/2(h) | 3.87/6.85 | | 3.40/5.59 | | 3.70/6.77 |
| AUC0-last (ng · h/mL) | 1100/3105 | 2.22/ 13.7 | 907/2592 | 94.4/ 79.6 | 915/2650 |

Studies show that the dominant crystalline form of Dositinib is crystalline form B. The crystalline form obtained by rapid crystallization or solvent evaporation is crystalline form A, or a mixed crystalline form of A and B. Under the same conditions, a mixture of crystalline forms A and B of AZD9291 is obtained (FIG. 8), and commercially purchased is also a mixture of crystalline forms A and B. The anticancer activity of Dositinib crystalline form B in HCC-827 nude mouse model was significantly higher than that of the active pharmaceutical ingredients of purchased Osimertinib (FIG. 8, mixture of crystalline forms A and B), and the former was twice that of the latter (FIG. 1). The pharmacokinetic results of animals showed that the bioavailability of the crystalline form B of Dositinib was 20% higher than that of the active pharmaceutical ingredients of AZD9291 with crystalline forms (FIGS. 2-5, Table 1). The higher bioavailability of the crystalline form B of Dositinib than the mixed crystalline forms of AZD9291 may be one of the reasons for its high anticancer activity.

The Cuk$\alpha$-X-ray diffraction (XRD) spectrum of the crystalline form B of Dositinib is shown in FIG. 7.

The following advantages are associated with the 2-(2,4,5-substituted phenylamino) pyrimidine derivative and the crystalline form B thereof of the disclosure. 1. The results of pharmacokinetic and pharmacodynamic studies show that compared with Osimertinib, the amount of the toxic metabolite of N-demethylation of indole of Dositinib or its crystalline form B is significantly reduced, and the pharmacodynamic effect is enhanced. 2. The bioavailability of the crystalline form B of Dositinib is better. Therefore, Dositinib is expected to be developed into a safer and more effective new drug for the treatment of non-small cell lung cancer with EGFR mutation.

DETAILED DESCRIPTION

Figure 1:
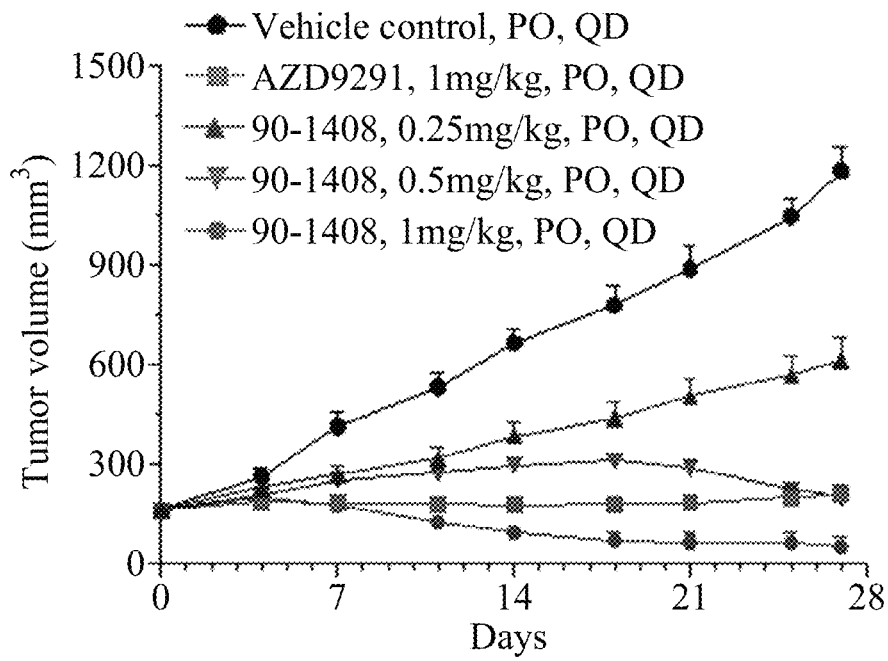
FIG. 1 shows a comparison of the anticancer activities of the crystalline form B of Dositinib and Osimertinib (HCC-827)
Figure 2:
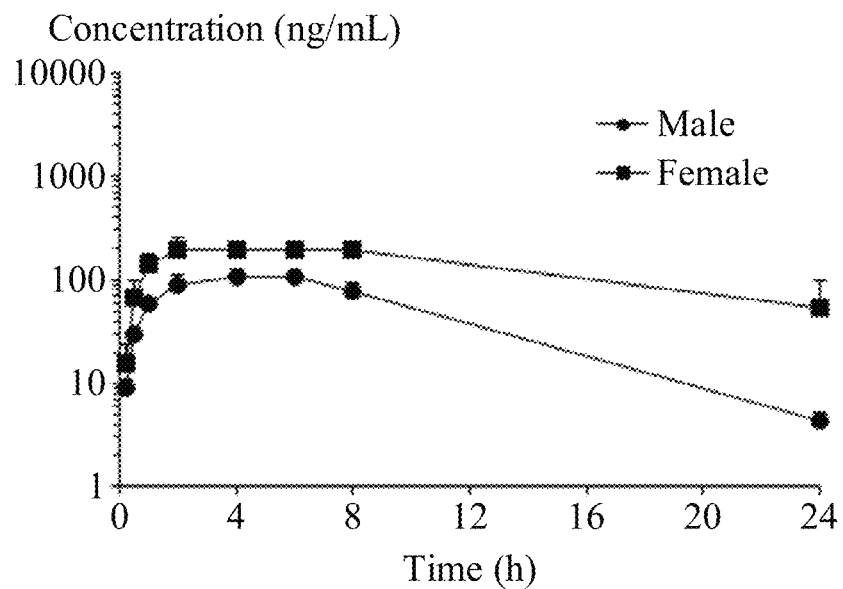
FIG. 2 shows a change of the mean concentration of Dositinib in plasma with time after intragastric administration of 12 mg/kg of Dositinib crystal form B in male and female mice.
Figure 3:
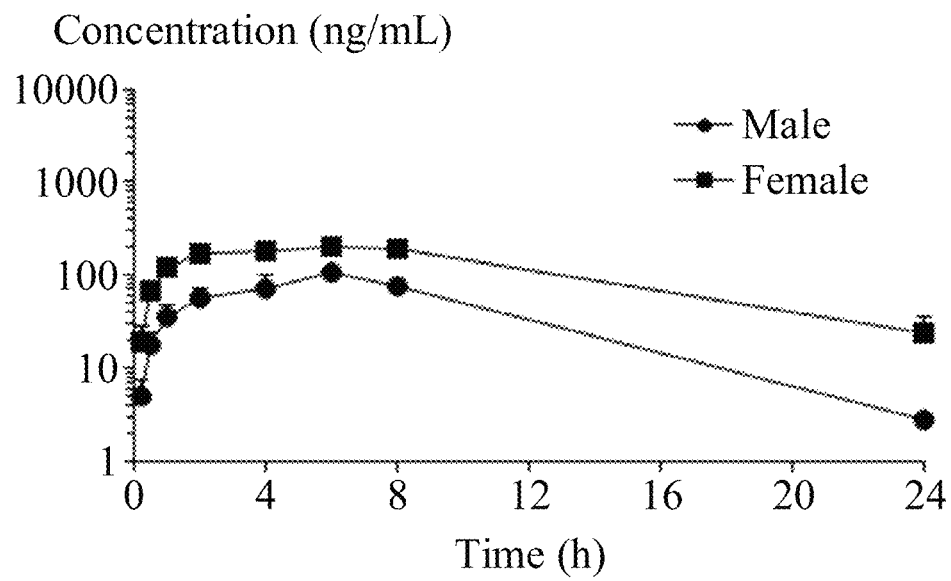
FIG. 3 shows a change of the mean concentration of Osimertinib in plasma with time after intragastric administration of 12 mg/kg of Osimertinib (AZD9291) in male and female mice.
Figure 4:
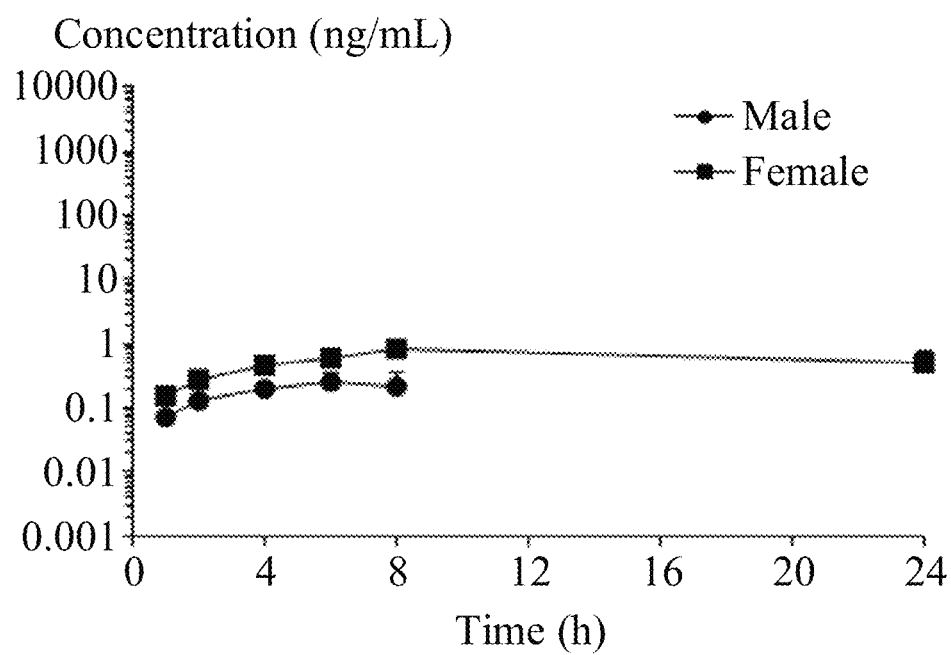
FIG. 4 shows a change of the mean concentration of AZ5104-D2 in plasma with time after intragastric administration of 12 mg/kg of Dositinib crystal form B in male and female mice.
Figure 5:
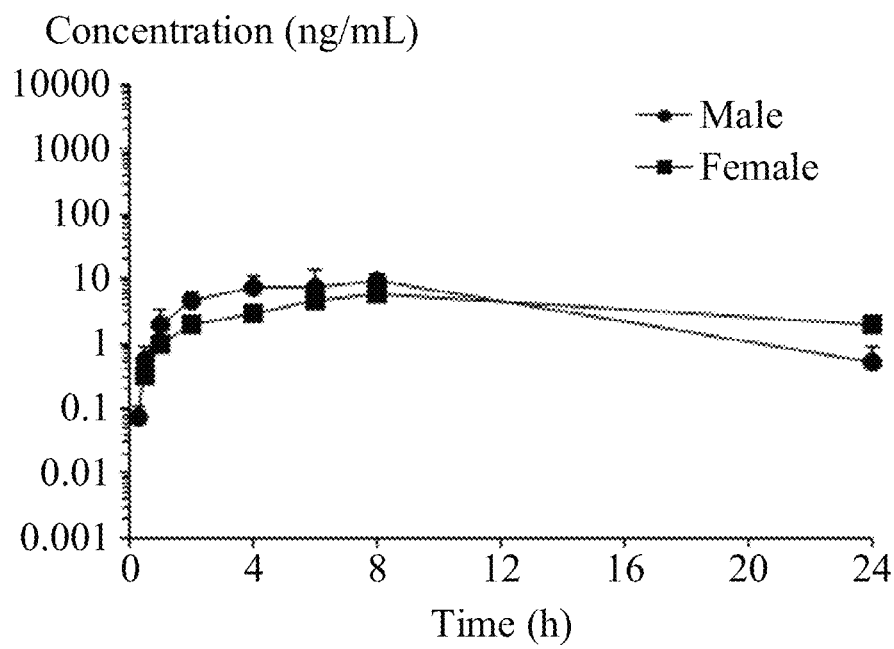
FIG. 5 shows a change of the mean concentration of AZ5104 in plasma with time after intragastric administration of 12 mg/kg of Osimertinib in male and female mice.
Figure 6:
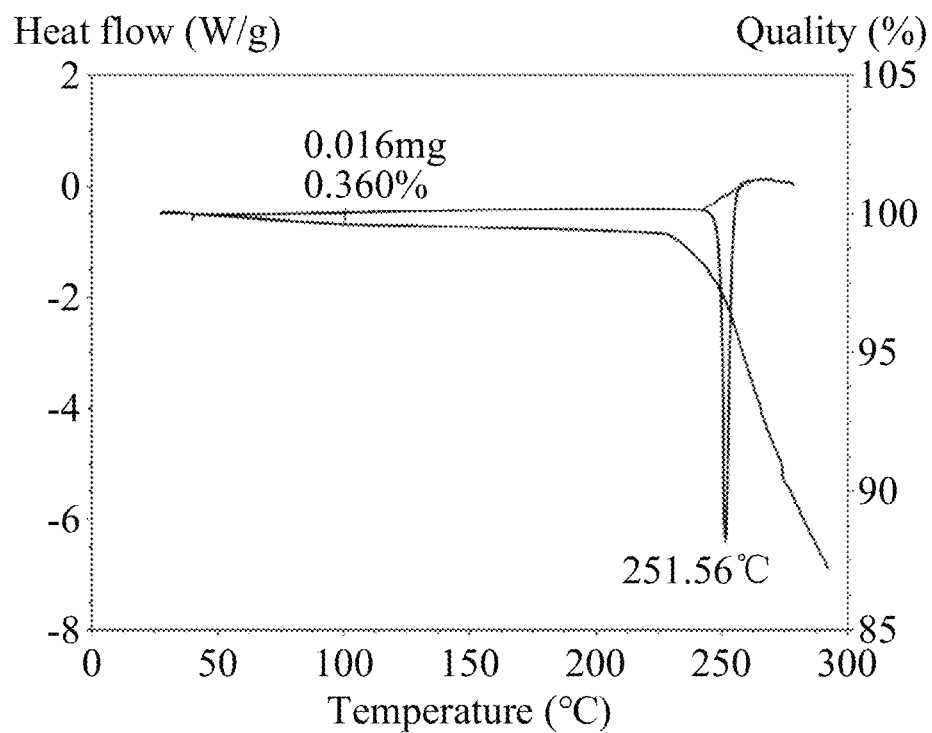
FIG. 6 shows the differential scanning calorimetry (DSC) and thermogravimetric analysis (TGA) spectra of the crystalline form B of Dositinib.
Figure 7:
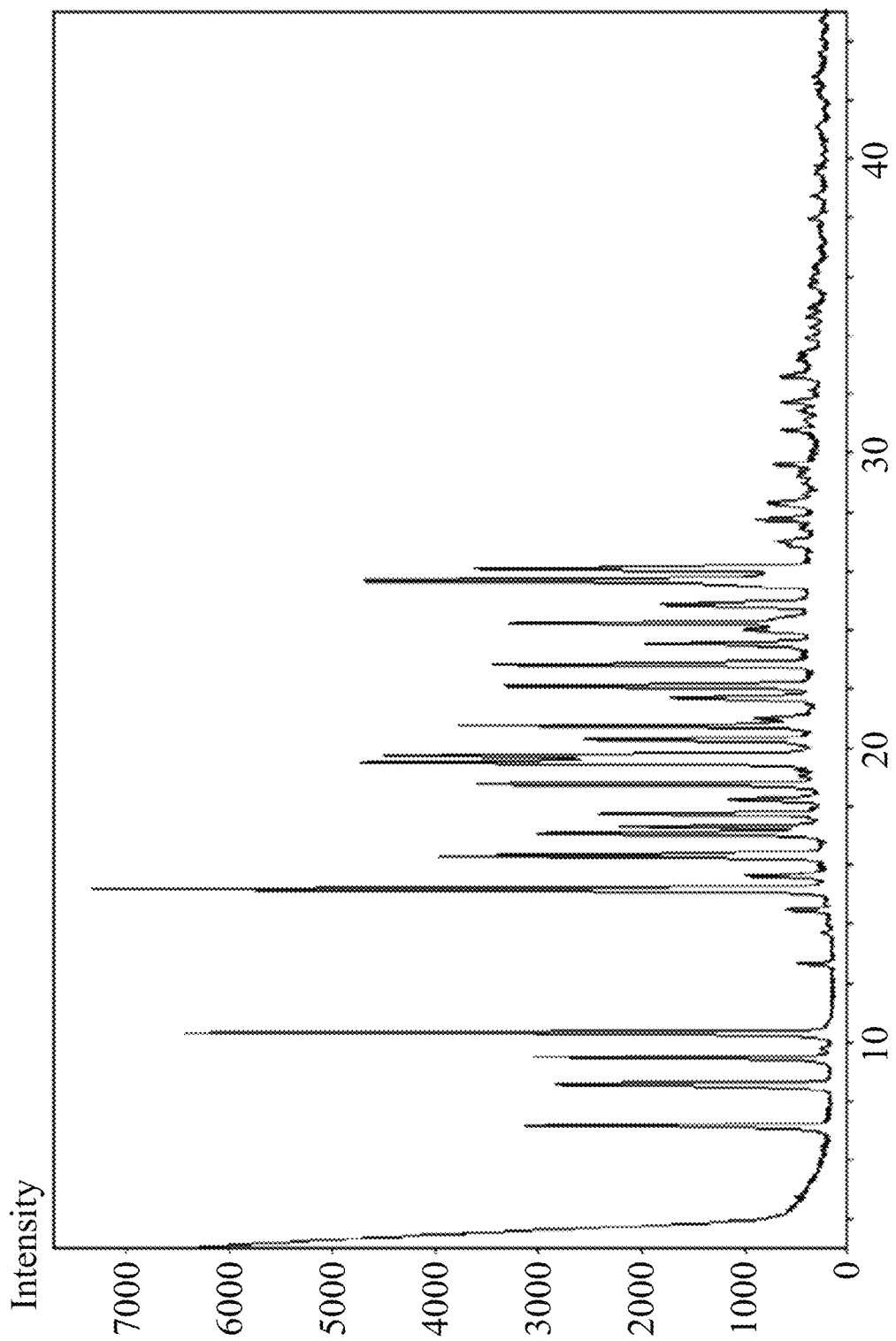
FIG. 7 shows Cuk$\alpha$-X-ray diffraction (XRD) spectrum of the crystalline form B of Dositinib.
Figure 8:
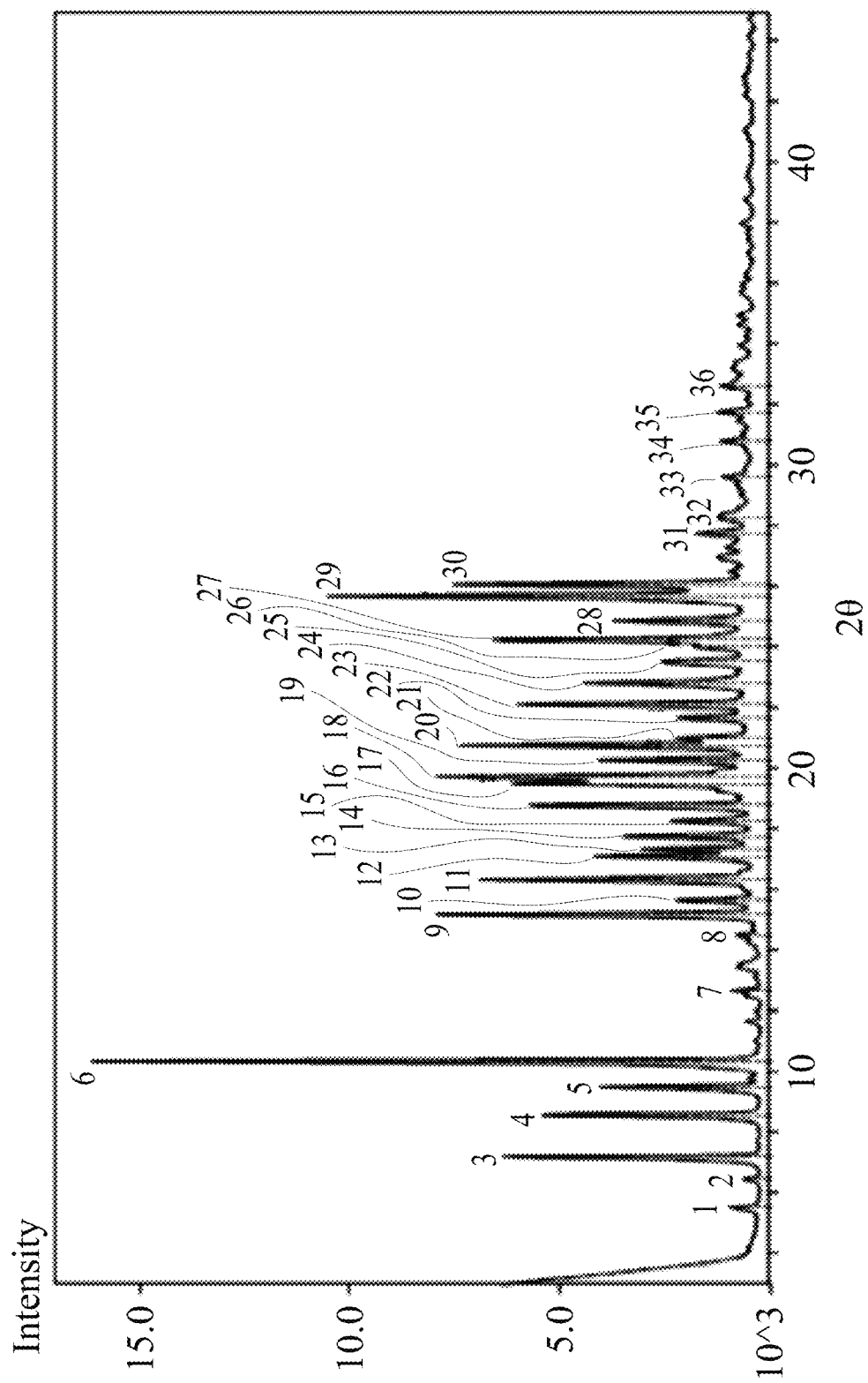
FIG. 8 shows Cuk$\alpha$-X-ray diffraction (XRD) spectrum of a mixed crystalline form of commercially purchased AZD9291.

To further illustrate, embodiments detailing a 2-(2,4,5-substituted phenylamino) pyrimidine derivative I and a crystalline form B thereof are described below. It should be noted that the following embodiments are intended to describe and not to limit the disclosure.

Example 1 Preparation of Intermediate 9

Step 1

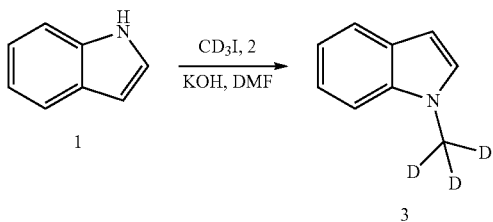

The compound 1 (2.00 kg, 1.71 mol) and KOH (1.44 kg, 25.6 mol) were added to a precooled DMF (6.0 L) at 0-15° C., and the mixture was stirred for 0.5 h. The compound 2 (2.47 kg, 17.1 mol) was dropwise added to the above mixture at 0-5° C. within 4 h. The reaction mixture was stirred at 0-10° C. for 2 h, and then stirred at 5-15° C. for 12 h. Thereafter, ice water (15.0 L) was added, and the resulting mixture was extracted with a mixture of petroleum ether (10 L) and methyl tert butyl ether (10.0 L). The organic phase was washed with brine, dried over $Na_2SO_4$, filtered and evaporated to remove the solvent to obtain an oily product (2.60 kg, 82% purity, containing solvent). $^1$H NMR (400 MHz, DMSO-d$_6$) δ ppm 6.41-6.48 (m, 1H); 6.96-7.03 (m, 1H); 7.03-7.05 (m, 1H); 7.11-7.17 (m, 1H); 7.24-7.26 (m, 1H); 7.55-7.57 (m, 1H).

Step 2

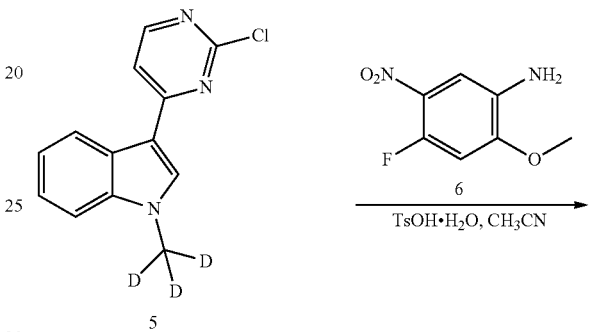

The compound 4 (2.42 kg, 16.24 mol), dimethyl ether (DME) (8.0 L) and anhydrous $FeCl_3$ (2.64 kg, 16.3 mol) were added to a reactor, where the reaction temperature was controlled at 10° C., and then heated to 60° C. A DME (2.0 L) solution of the compound 3 (2.18 kg, 16.2 mol) was added to the mixture and stirred for 2 hours. Thereafter, methanol (5.0 L) and water (10 L) were successively added to the reaction mixture at 10-30° C., stirred for 0.5 h, and filtered to obtain a first red solid (6 kg). The first red solid was mixed with acetonitrile (12.0 L) and water (24.0 L), stirred, and filtered to obtain a second red solid (4 kg). Then the second red solid was mixed with acetonitrile (5.0 L), stirred for 1 h, filtered and dried to obtain a compound 5 (2.14 kg, 54%). $^1$H NMR (400 MHz, DMSO-d$_6$) δ ppm 7.20-7.36 (m, 2H); 7.58 (br d, J=7.70 Hz, 1H); 7.82 (d, J=5.38 Hz, 1H); 8.41 (br d, J=7.58 Hz, 1H); 8.47-8.57 (m, 2H).

Step 3

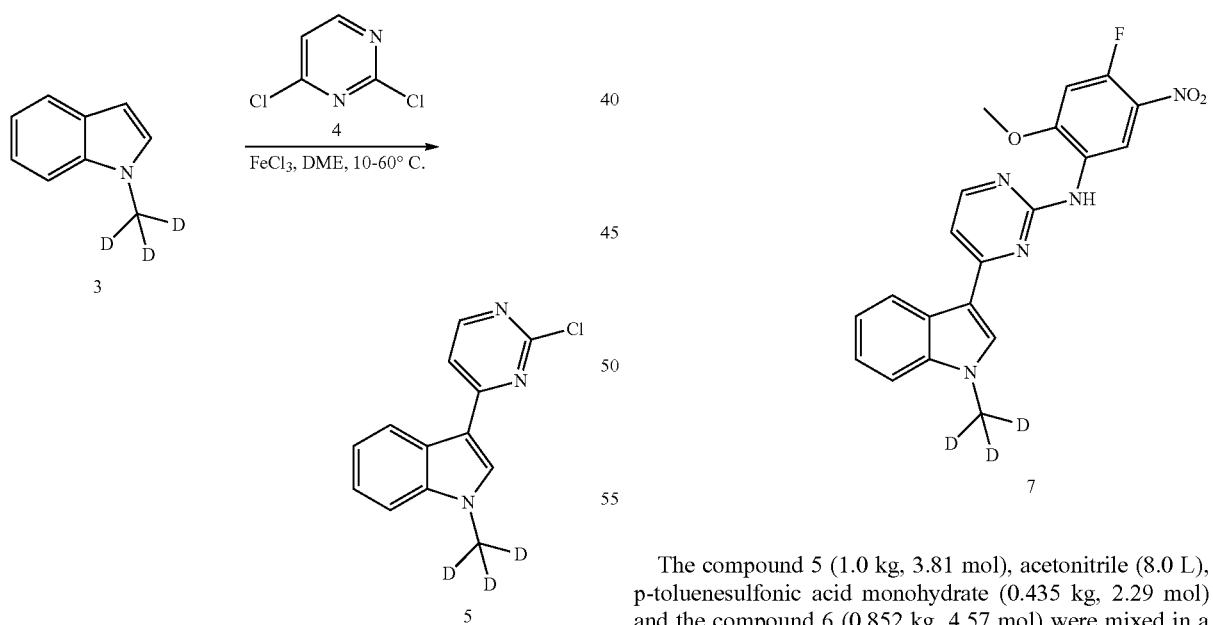

The compound 5 (1.0 kg, 3.81 mol), acetonitrile (8.0 L), p-toluenesulfonic acid monohydrate (0.435 kg, 2.29 mol) and the compound 6 (0.852 kg, 4.57 mol) were mixed in a reactor, stirred at 80° C. for 12 h, cooled to 20° C. and filtered. The resulting solid was washed with acetonitrile (3.0 L×6) and dried in air to obtain a yellow solid 7 (1.2 kg, 85%). 1H NMR (400 MHz, DMSO-d6) δ ppm 4.00 (s, 3H); 7.09-7.17 (m, 1H); 7.31 (t, J=7.64 Hz, 1H); 7.40-7.52 (m, 2H); 7.59 (d, J=8.19 Hz, 1H); 8.09-8.40 (m, 2H); 8.49-8.69 (m, 1H); 8.83 (br d, J=7.83 Hz, 1H).

Step 4

Example 2 Preparation of Compound 12

Step 1

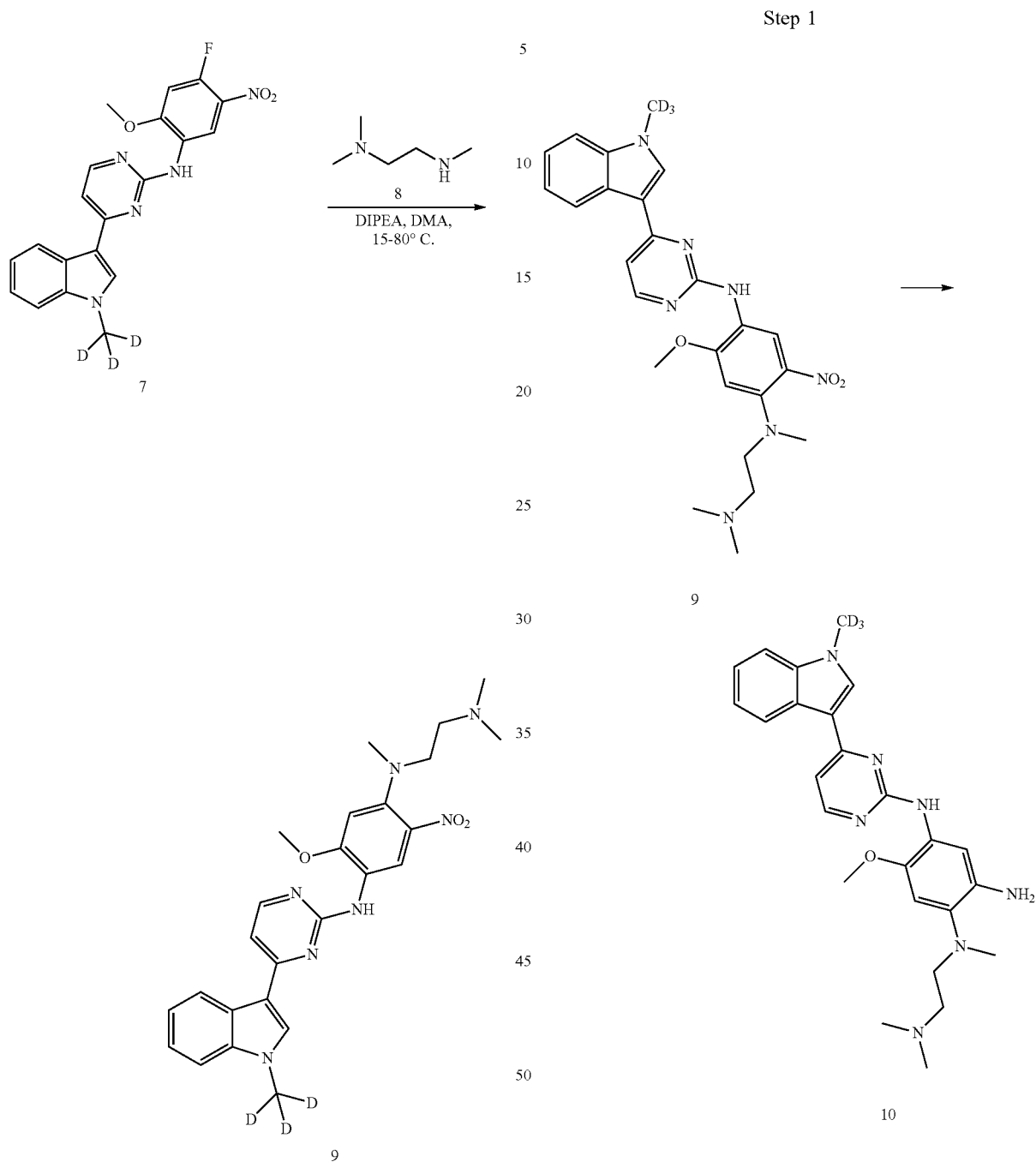

The compound 7 (3.60 kg, 8.81 mol), diisopropyl ethylamine (DIPEA) (1.76 kg, 13.6 mol), and DMA (14.4 L) were mixed with the compound 8 (1.11 kg, 10.9 mol) at 15° C. The reaction mixture was stirred at 80° C. for 12 h, and then ethyl cyanide (21.6 L) was added, cooled to 20° C., to yield a red solid. The red solid was filtered, washed with ethyl cyanide (12 L), to yield a solid 9 (3.45 kg, 81%). 1H NMR (400 MHz, DMSO-d6) δ ppm 2.16 (s, 6H) 2.44-2.48 (m, 2H) 2.86 (s, 3H) 3.26 (t, J=6.85 Hz, 2H) 3.95 (s, 3H) 6.85 (s, 1H) 7.11 (t, J=7.52 Hz, 1H) 7.18-7.29 (m, 2H) 7.52 (d, J=8.07 Hz, 1H) 8.09 (s, 1H) 8.27-8.42 (m, 3H) 8.62 (s, 1H).

The compound 9 (2.39 g, 5 mmol), MeOH (200 ml), ammonium formate (2.39 g) and palladium carbon (200 mg, 5%) were successively added into a single mouth bottle. The reaction mixture was stirred under a hydrogen balloon for 16 h, and filtered. The filtrate was concentrated to dry, water (100 mL) was added, and the pH was adjusted to 9 with saturated sodium bicarbonate solution. The mixture was extracted with DCM (3×100 mL). The organic phases were combined, dried over $Na_2SO_4$, filtered, and evaporated to remove the solvent to give a white solid 10 (2.05 g, 91%). 1H-NMR (400 MHz, DMSO-d6) δ 2.18 (s, 6H), 2.36 (t, J=6.8 Hz, 2H), 2.64 (s, 3H), 2.89 (t, J=6.8 Hz, 2H), 3.75 (s, 3H), 4.58 (br s, 2H), 6.77 (s, 1H), 7.23-7.27 (m, 3H), 7.50-7.53 (m, 2H), 7.79 (s, 1H), 8.28 (d, J=5.2 Hz, 1H), 8.30 (s, 1H), 8.43 (d, J=8.0 Hz, 1H). LCMS (M+1)+: 449.3.

Step 2

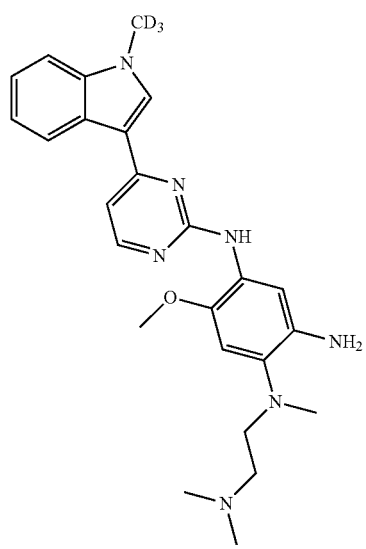

10

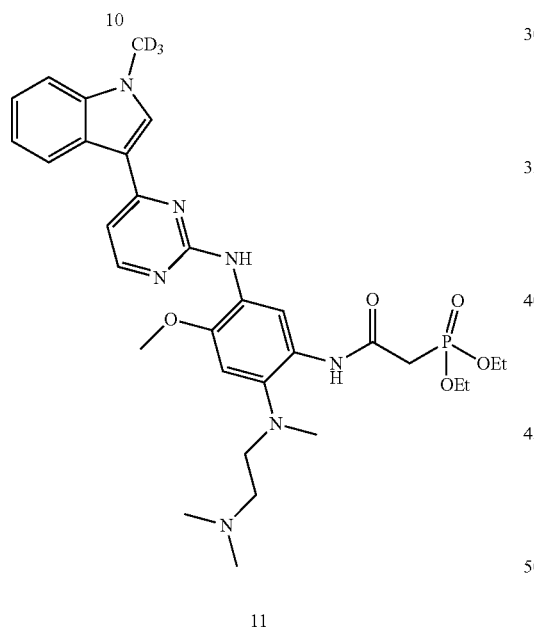

11

The compound 10 (4.93 g, 0.011 mol), diethylphosphoacetic acid (2.35 g, 0.012 mol) and N, N-diisopropyl ethylamine (1.68 g, 0.013 mol) were dissolved in tetrahydrofuran (25 mL), and HATU (4.94 g, 0.013 mol) was slowly added. The mixture was stirred at 25° C. for 5 hours. The reaction solution was poured into water (50 mL) and extracted with ethyl acetate (50 mL 2). The organic phases were combined. The organic phase was washed with secondary water (50 mL×4) and semi saturated salt water (50 mL 4) in sequence, dried with anhydrous Na$_2$SO$_4$, concentrated to obtain a light yellow solid 11 (4.93 g, yield 71.5%), which was directly used in the next reaction without purification. $^1$HNMR (400 MHz, DMSO-d$_6$): δ 1.26 (t, J=7.2 Hz, 6H), 2.20 (s, 6H), 2.31 (m, 2H), 2.70 (s, 3H), 2.94 (m, 2H), 3.12, 3.17 (ss, 2H), 3.84 (s, 3H), 4.11 (q, J=7.2 Hz, 4H), 7.02 (s, 1H), 7.16-7.27 (m, 3H), 7.53 (d, J=7.2 Hz, 1H), 7.92 (s, 1H), 8.23 (d, J=8.0 Hz, 1H), 8.31 (d, J=5.2 Hz, 1H), 8.62 (s, 1H), 8.97 (br, 1H), 9.86 (s, 1H). LCMS (M+1)+: 627.3.

Step 3

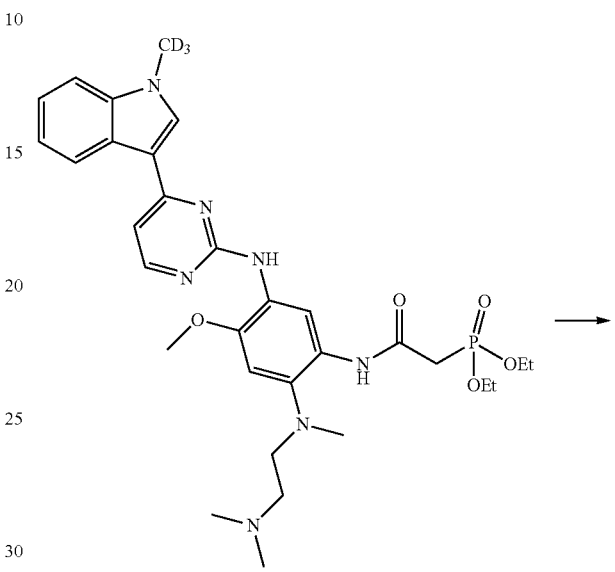

11

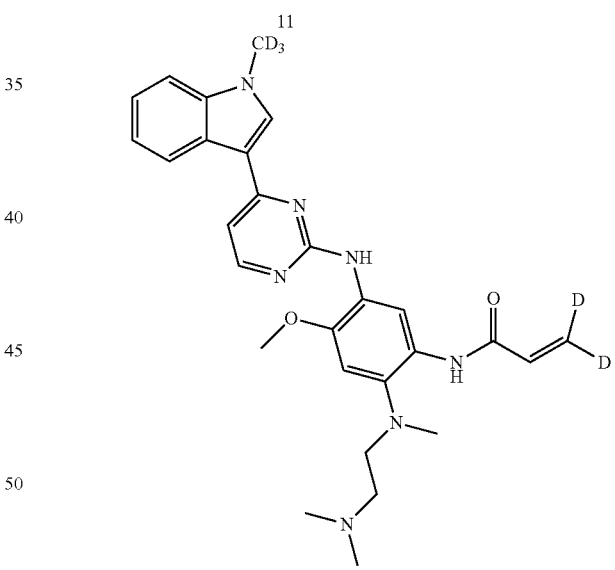

12

The compound 11 (100 mg, 0.16 mmol), (CD$_2$O)$_n$ (5 mg, 0.05 mmol), lithium chloride (10 mg, 0.24 mmol) and potassium hydroxide (27 mg, 0.48 mmol) were dissolved in THF/H$_2$O (1 mL/0.5 mL) solution and stirred at room temperature overnight (16 h). Water (5 mL) was added to the reaction solution. The mixed solution was extracted with ethyl acetate (10 mL), and washed with water (5 mL×2) and salt water (10 mL 2) in sequence. The organic phase was dried with anhydrous sodium sulfate and concentrated to obtain a crude product (90 mg). The crude product was purified with column chromatography (eluent: dichloromethane:methanol=10:1) to obtain a light yellow solid 12 (50 mg, yield 62%). $^1$HNMR (400 MHz, DMSO-$d_6$): δ 2.24 (s, 6H), 2.30 (br, 2H), 2.72 (s, 3H), 2.89 (br, 2H), 3.87 (s, 3H), 6.43 (s, 1H), 7.05 (s, 1H), 7.16 (m, 1H), 7.24 (m, 2H), 7.53 (d, J=8.4 Hz, 1H), 7.89 (s, 1H), 8.24 (d, J=7.6 Hz, 1H), 8.33 (d, J=5.2 Hz, 1H), 8.68 (s, 1H), 9.16 (s, 1H), 10.20 (br, 1H). LCMS (M+1)$^+$: 505.3.

Example 3 Preparation of Crystalline Form B of Compound I

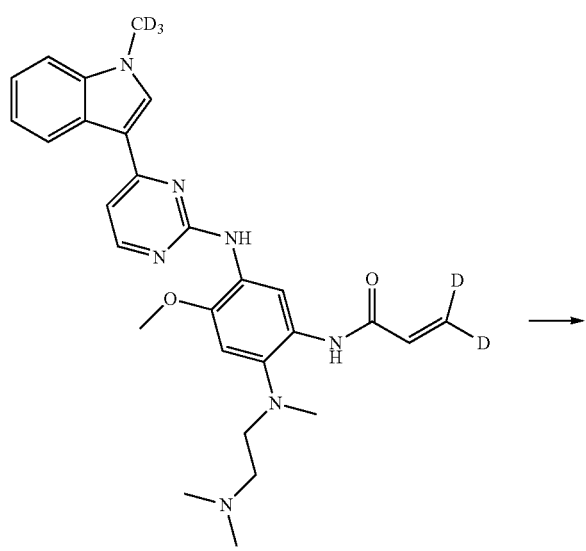

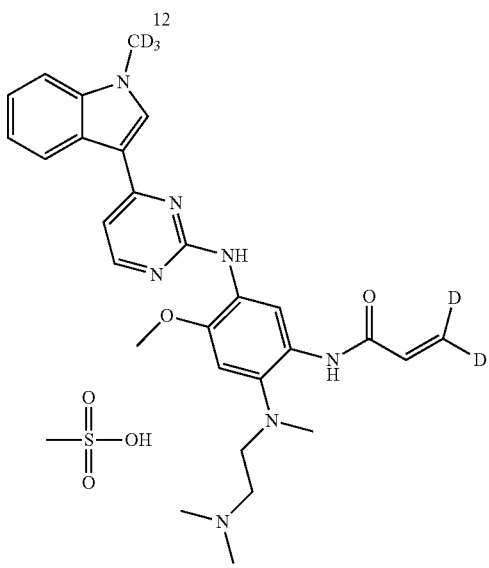

I

The compound 12 (5.04 g, 10 mmol) was mixed with acetone (55 mL) and water (5 mL) was added at 50° C. Methylsulfonic acid (0.94 g, 9.8 mmol) was dropwise added to the reaction solution and stirred at 50° C. for 1 h to precipitate a solid. The solution was cooled to room temperature, filtered, and the resulting solid was washed with acetone (5 mL) and vacuum dried at 25° C. to obtain a solid product (5.5 g, 91%). $^1$HNMR (400 MHz, DMSO-$d_6$): δ 2.72, 2.75 (ss, 6H), 2.90 (s, 6H), 3.29 (m, 2H), 3.50 (m, 2H), 4.03 (s, 3H), 6.56 (s, 1H), 6.99 (s, 1H), 7.21 (m, 3H), 7.46 (d, J=8.0 Hz, 1H), 8.17 (s, 1H), 8.26 (d, J=5.6 Hz, 1H), 8.35 (d, J=7.6 Hz, 1H), 8.67 (s, 1H). LCMS (M+1)$^+$: 505.3.

The characterization data of single crystal B of the compound I are shown below:

| 2θ | Intensities % |
| --- | --- |
| 7.15 | 41.4 |
| 8.55 | 37.3 |
| 9.47 | 40.3 |
| 10.31 | 88 |
| 12.65 | 4.7 |
| 14.47 | 5.6 |
| 15.17 | 100.0 |
| 15.61 | 10.7 |
| 16.29 | 52.4 |
| 17.07 | 38.5 |
| 17.31 | 27.3 |
| 17.73 | 30.1 |
| 18.22 | 12.1 |
| 18.74 | 45.3 |
| 19.47 | 61.3 |
| 19.70 | 57.6 |
| 20.24 | 30.2 |
| 20.72 | 47.8 |
| 21.68 | 19.2 |
| 22.08 | 41.6 |
| 22.80 | 43.1 |
| 23.50 | 22.1 |
| 23.99 | 8.6 |
| 24.20 | 40.6 |
| 24.83 | 19.8 |
| 25.65 | 60.4 |
| 26.15 | 45.5 |
| 26.99 | 4.6 |
| 27.69 | 7.3 |
| 28.30 | 5.8 |
| 29.57 | 5.6 |
| 30.74 | 4.2 |
| 32.58 | 5.0 |

Example 4 Preparation of Product with a Mixed Crystalline Form

The compound 12 or AZD9291 (1 mmol) was dissolved in ethanol (6 mL) at 50° C., and then a mixed solution of methylsulfonic acid (1 mmol) and ethylate (2 mL) was added, stirred for 0.5 h, cooled to room temperature, filtered, washed with petroleum ether, and air-dried to obtain a product with a mixed crystalline form.

Example 5 In Vivo Pharmacodynamics of Crystalline Form B of Dositinib and AZD9291 on Human Non-Small Cell Lung Cancer HCC827 Cell Subcutaneous Xenograft BALB/C Nude Mouse Model Cell Culture:

Human non-small cell lung cancer HCC827 (ATCC-CRL-2868) was monolayer cultured in vitro. The culture conditions were: RPMI-1640 medium with 10% fetal bovine serum, 100 U/mL penicillin and 100 g/mL streptomycin, in a 5% $CO_2$ incubator at 37° C. Trypsin EDTA was used for routine digestion twice a week. When the cell saturation was 80%-90% and the number reached the requirements, the cells were collected, counted and transplanted.

Animals: BALB/c nude mouse, female, 6-8 weeks old, weight 18-22 g. A total of 60 (40+50%) was purchased from Shanghai Sippr-BK Lab. Animal Co. Ltd or other companies.

Tumor transplantation: 0.2 mL ($1\times10^7$) HCC827 cells (with matrix glue, volume ratio 1:1) were subcutaneously transplanted to the right back of each mouse, and each group was administered when the average tumor volume reached 150-200 mm$^3$. Experimental grouping and administration schedule are shown in the table below.

| Experimental grouping and dose schedule | | | | | |
|---|---|---|---|---|---|
| Groups | N[1] | Compounds | Dosage (mg/kg) | Dosing volume (μL/g)[2] | Administration mode | Administration frequency |
| 1 | 8 | Solvent for control group | — | 10 | PO | QD |
| 2 | 8 | AZD9291 | 1 | 10 | PO | QD |
| 3 | 8 | Crystalline form B of Dositinib | 0.25 | 10 | PO | QD |
| 4 | 8 | Crystalline form B of Dositinib | 0.5 | 10 | PO | QD |
| 5 | 8 | Crystalline form B of Dositinib | 1 | 10 | PO | QD |

Notes:
1. N: Number of mice per group;
2. Dosing volume: 10 μL/g according to the weight of mice. If the weight loss exceeds 15%, the dose schedule shall be adjusted accordingly.

Experimental index: to investigate whether the tumor growth is inhibited, delayed or cured. The tumor diameter was measured with a vernier caliper twice a week. The calculation formula of tumor volume is: $V=0.5a\times b^2$, a and b represent the long diameter and short diameter of the tumor, respectively.

The antitumor effect of the compound was evaluated by tumor growth inhibition value (TGI) (%) or relative tumor proliferation rate T/C (%). TGI (%) reflects the tumor growth inhibition rate.

Calculation of TGI (%): TGI (%)=((1−(average tumor volume at the end of administration in a treatment group−average tumor volume at the beginning of administration in the treatment group))/(average tumor volume at the end of treatment in the solvent control group−average tumor volume at the beginning of treatment in the solvent control group))×100%.

Relative tumor proliferation rate T/C (%): the calculation is as follows: T/C %=$T_{RTV}/C_{RTV}\times100\%$ ($T_{RTV}$: treatment group RTV; $C_{RTV}$: negative control group RTV). The relative tumor volume (RTV) is calculated according to the results of tumor measurement. The calculation formula is RTV=$V_t/V_0$, where $V_0$ is the average tumor volume measured in a group at the beginning of administration (i.e. $D_0$), $V_t$ is the average tumor volume measured in a certain measurement, and Trtv and $C_{RTV}$ are taken in the same day.

At the end of the experiment, the tumor weight is measured and the percentage of $T_{weight}/C_{weight}$ is calculated. $T_{weight}$ and $C_{weight}$ represent the tumor weight of the administration group and the control group, respectively.

Data analysis: T-test was used for comparison between the two groups. One-way ANOVA was used for comparison among three or more groups. If there were significant differences in F values, multiple comparisons should be made after ANOVA analysis. All data were analyzed with SPSS 17.0. P<0.05 was considered as significant difference.

The pharmaceutical results are shown in FIG. 1. The anticancer activity of 0.5 mg/kg of the crystalline form B of Dositinib (code 90-1408) in nude mice HCC-827 model was equivalent to 1 mg/kg of AZD9291. The results showed that the anticancer activity of the crystalline form B of Dositinib in this model was twice that of AZD9291.

Example 6 Pharmacokinetics of Dositinib and AZD9291

1. Preparation of Test Solution
1) Preparation of preparations for intravenous administration
   a. Weigh an appropriate amount of compound powders into a container;
   b. Add a certain volume of D5W (5% glucose by mass) aqueous solution to the container, whirl or stir until a clear solution was obtained (heating method can be used to help dissolution if necessary);
   c. Add the remaining volume of D5W (5% glucose) aqueous solution, whirl or stir until the solution was clear. The prepared intravenous preparation was filtered with a 0.22 μm microporous membrane, and stored in a dark place at 2° C. to 8° C. The intravenous preparation was prepared on the day of administration, and then analyzed for use.
2) Preparation of Orally Administered Preparations
   a) Weigh an appropriate amount of compound powders into a container;
   b) Add an appropriate volume of 0.5% HPMC (hydroxypropyl methylcellulose, 4000 CP) aqueous solution to the container, and continuously stir or whirl until a uniform solution was obtained;
   c) Add the remaining volume of 0.5% HPMC (hydroxypropyl methylcellulose, 4000 CP) aqueous solution to the container to a final volume, and continuously stir or whirl until the solution was uniform.

The preparation for intragastric administration was prepared the day before administration and analyzed. When the preparation was not in use, it was stored in a refrigerator at 2° C. to 8° C. and used within 8 days.

Animal: Rats (SD) from Beijing Vital River Laboratory Animal Technology Co., Ltd. 36 rats (18 males and 18 females), 6-10 weeks old, 200-300 g (males); 170-280 g (female). On the first day of the test, the animals in the first group were administered with the crystalline form B of Dositinib solution (code 90-1408) by single injection through caudal vein; the animals in the groups 2, 3 and 4 were administered with different doses of the crystalline form B of Dositinib solution (code 90-1408) orally by gavage. The animals in the fifth group were administered with different doses of the crystalline form B of Dositinib solution (code 90-1408) by gavage once a day for 7 consecutive days, with a dose volume of 10 mL/kg. The animals in the sixth group were administered with AZD9291 (mesylate) solution by gavage, with a dose volume of 10 mL/kg. The blood samples were taken at the following time points after administration to measure the blood drug concentrations: 0.083, 0.25, 0.5, 1, 2, 4, 6, 8, 12 and 24 hours.

Administration: Whole blood samples were collected through jugular vein puncture (or other appropriate blood collection sites) at the specified time (about 0.15 mL in the fifth group and 0.23 mL in other groups), with wet ice operation throughout the whole process, and the actual blood collection time was recorded in the experimental records. The acceptable error of collection time point was ±1 minute within 1 hour of administration, and ±5% of theoretical time for other time points. The blood samples were immediately transferred to labeled commercial tubes containing K₂-EDTA and then centrifuged (3,000 g, 4° C., 15 min) for plasma collection. The plasma was transferred to a centrifuge tube, quick-frozen in dry ice, and stored in a cryogenic refrigerator at −60° C. or lower for LC-MS/MS analysis (mother drug and its metabolites were analyzed in the groups 1-4 and 6, only the mother drug was analyzed in the fifth group).

Plasma samples: the concentrations of the crystalline form B of Dositinib and AZD9291 and their metabolites AZ5104-D2 and AZ5104 in plasma were determined by the bioanalysis department of Shanghai Pharmatechs Co. Ltd. through high performance liquid chromatography-mass spectrometry (LC-MS/MS).

Retention time, chromatogram collection and chromatogram integration of compounds and internal standards were processed by Software Analyst (Applied Biosystems), and data statistics were processed by software Watson LIMS (Thermo Fisher Scientific) or Analyst (Applied Biosystems). The unit of the analyte concentration in the sample was nM, three significant figures were reserved, and all values expressed in percentage (such as % deviation and % coefficient of variation, etc.) were reserved to one decimal place.

Data analysis and reporting: WinNonlin™ Version 6.3 (Pharsight, Mountain View, CA) or above pharmacokinetic software for non-atrioventricular models was used to process the blood drug concentration, and the linear logarithm trapezoid method was used to calculate the pharmacokinetic parameters.

Through preclinical animal pharmacokinetic and pharmacodynamic studies, it was found that the bioavailability of the crystalline form B of Dositinib was 20% higher than that of AZD9291 of mixed crystalline forms (see Table 1), which was conducive to improving the anti-lung cancer efficacy of Dositinib. In addition, the production of the metabolite AZ5104-2D of N-demethylation of indole of Dositinib was 98% (male) and 83% (female) lower than that of AZ5104 of Osimertinib (see FIGS. 2-5 and Table 1), which was conducive to reducing the toxic and side effects caused by inhibiting wild EGFR. Compared with Osimertinib, Dositinib may have obvious clinical advantages in the efficacy and safety of treating non-small cell lung cancer.

What is claimed is:

1. A crystalline form B of a 2-(2,4,5-substituted phenylamino) pyrimidine derivative of formula I:

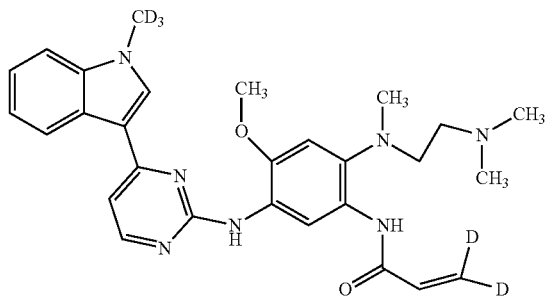 [SMILES: [2H]C([2H])=CC(=O)Nc1cc(Nc2nccc(-c3cn(C([2H])([2H])[2H])c4ccccc34)n2)c(OC)cc1N(C)CCN(C)C]

wherein a CuKα-X-ray powder diffraction (XRPD) spectrum of the crystalline form B comprises diffraction peaks at diffraction angle 2θ positions of 8.55°±0.2°, 9.47°±0.2°, 10.31°±0.2°, 12.65°±0.2°, 14.47°±0.2°, 15.17°±0.2°, 15.61°±0.2°, 16.29°±0.2°, 17.07°±0.2°, 17.31°±0.2°, 17.73°±0.2°, 18.22°±0.2°, 18.74°±0.2°, 19.47°±0.2°, 19.70°±0.2°, 20.24°±0.2°, 20.72°±0.2°, 21.68°±0.2°, 22.08°±0.2°, 22.80°±0.2°, 23.50°±0.2°, 23.99°±0.2°, 24.20°±0.2°, 24.83±0.2°, 25.65°±0.2°, 26.15±0.2°, 26.99°±0.2°, 27.69°±0.2°, 28.30°±0.2°, 29.57°±0.2°, 30.74°±0.2°, and 32.58°±0.2°.

2. A method of treatment of non-small cell lung cancer, the method comprising administering to a patient in need thereof an effective amount of the crystalline form B of the 2-(2,4,5-substituted phenylamino) pyrimidine derivative of claim 1.

3. The method of claim 2, wherein the method further comprises administering to the patient another lung cancer therapeutic drug.

* * * * *